United States Patent
WasDyke et al.

(10) Patent No.: US 7,959,645 B2
(45) Date of Patent: Jun. 14, 2011

(54) RETRIEVABLE VENA CAVA FILTER

(75) Inventors: Joel M. WasDyke, Eden Prairie, MN (US); Jay Rassat, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 406 days.

(21) Appl. No.: 10/980,579

(22) Filed: Nov. 3, 2004

(65) Prior Publication Data
US 2006/0095068 A1    May 4, 2006

(51) Int. Cl.
*A61F 2/01* (2006.01)
(52) U.S. Cl. ........................................ 606/200
(58) Field of Classification Search .............. 606/200, 606/113, 114, 127
See application file for complete search history.

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,580,568 A | 4/1986 | Gianturco | |
| 4,643,184 A * | 2/1987 | Mobin-Uddin | 606/200 |
| 4,688,553 A | 8/1987 | Metals | |
| 4,781,177 A | 11/1988 | Lebigot | |
| 4,817,600 A | 4/1989 | Herms et al. | |
| 4,957,501 A | 9/1990 | Lahille et al. | |
| 4,969,891 A | 11/1990 | Gowortz | |
| 5,059,205 A | 10/1991 | El-Nounou et al. | |
| 5,071,407 A | 12/1991 | Termin et al. | |
| 5,108,418 A * | 4/1992 | Lefebvre | 606/200 |
| 5,133,733 A | 7/1992 | Rasmussen et al. | |
| 5,152,777 A | 10/1992 | Goldberg et al. | |
| 5,160,342 A | 11/1992 | Roger et al. | |
| 5,234,458 A | 8/1993 | Metais | |
| 5,300,086 A | 4/1994 | Gory et al. | |
| 5,329,942 A | 7/1994 | Gunther et al. | |
| 5,344,427 A | 9/1994 | Cottenceau et al. | |
| 5,350,398 A | 9/1994 | Pavcnik | |
| 5,370,657 A | 12/1994 | Irie | |
| 5,383,887 A | 1/1995 | Nadal | |
| 5,549,626 A | 8/1996 | Miller et al. | |
| 5,709,704 A * | 1/1998 | Nott et al. | 606/200 |
| 5,827,324 A | 10/1998 | Cassell et al. | |
| 5,836,969 A | 11/1998 | Kim et al. | |
| 5,893,869 A | 4/1999 | Barnhart et al. | |
| 6,126,673 A | 10/2000 | Kim et al. | |
| 6,156,055 A | 12/2000 | Ravenscroft | |
| 6,168,579 B1 | 1/2001 | Tsugita | |
| 6,171,328 B1 | 1/2001 | Addis | |
| 6,179,859 B1 | 1/2001 | Bates et al. | |
| 6,217,600 B1 * | 4/2001 | DiMatteo | 606/202 |
| 6,231,589 B1 | 5/2001 | Wessman et al. | |

(Continued)

FOREIGN PATENT DOCUMENTS

WO    95/18582 A1    7/1995

(Continued)

*Primary Examiner* — Ryan J Severson
(74) *Attorney, Agent, or Firm* — Seager, Tufte & Wickhem LLC

(57) ABSTRACT

A filter device positionable within a blood vessel for trapping emboli in the vessel, the filter device having a head and a plurality of divergent legs each secured at a first end to the head; each leg having one or more hooks at a second end. The hooks can include an expandable and contractible sleeve or hook that provides securing means for the legs and which also allows for easy removal of the filter device.

16 Claims, 5 Drawing Sheets

U.S. PATENT DOCUMENTS

| | | |
|---|---|---|
| 6,241,746 B1 | 6/2001 | Bosma et al. |
| 6,267,776 B1 | 7/2001 | O'Connell |
| 6,391,045 B1 | 5/2002 | Kim et al. |
| 6,436,120 B1 | 8/2002 | Meglin |
| 6,436,121 B1 | 8/2002 | Blom |
| 6,443,971 B1 | 9/2002 | Boylan et al. |
| 6,482,222 B1 | 11/2002 | Bruckheimer et al. |
| 6,485,501 B1 | 11/2002 | Green |
| 6,491,698 B1 | 12/2002 | Bates et al. |
| 6,506,205 B2 | 1/2003 | Goldberg et al. |
| 6,511,496 B1 | 1/2003 | Huter et al. |
| 6,511,503 B1 | 1/2003 | Burkett et al. |
| 6,517,559 B1 | 2/2003 | O'Connell |
| 6,582,447 B1 | 6/2003 | Patel et al. |
| 6,706,054 B2 | 3/2004 | Wessman et al. |
| 6,712,834 B2 | 3/2004 | Yassour et al. |
| 6,726,621 B2 | 4/2004 | Suon et al. |
| 2002/0193828 A1 | 12/2002 | Griffin et al. |
| 2003/0208253 A1 | 11/2003 | Boyer et al. |
| 2004/0082966 A1 | 4/2004 | WasDyke |
| 2004/0158273 A1* | 8/2004 | Weaver et al. ................ 606/200 |
| 2004/0158274 A1 | 8/2004 | WasDyke |
| 2004/0186510 A1* | 9/2004 | Weaver ......................... 606/200 |

FOREIGN PATENT DOCUMENTS

| | | |
|---|---|---|
| WO | 00/18467 A1 | 4/2000 |
| WO | 2004/024032 A1 | 3/2004 |

\* cited by examiner

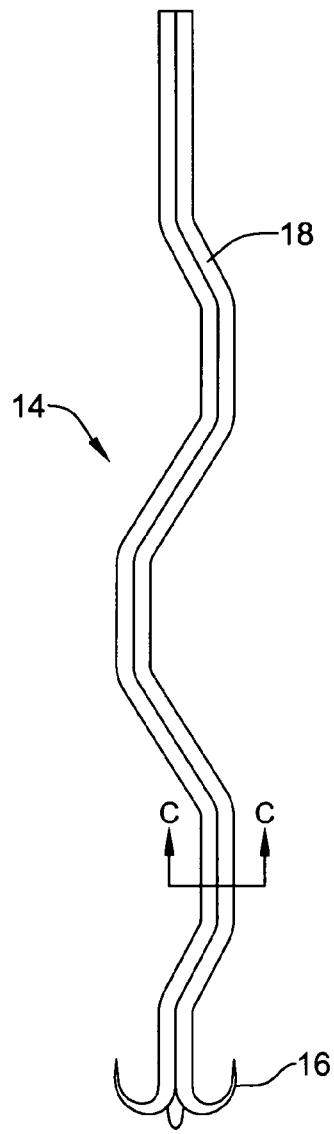
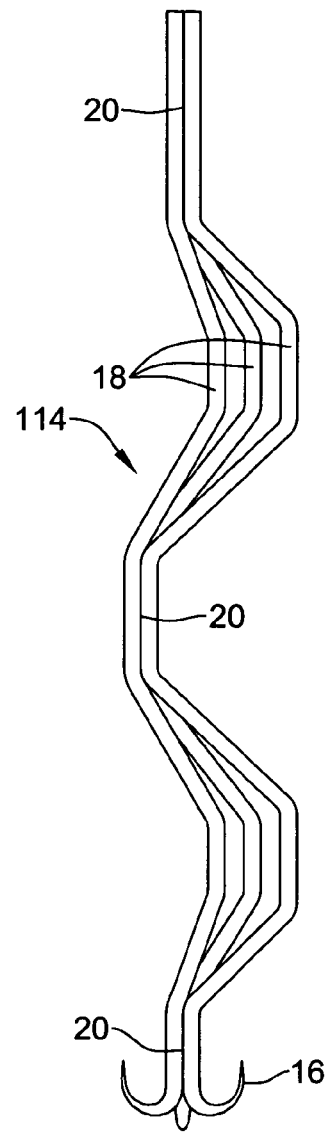
Figure 2A　　　　Figure 2B
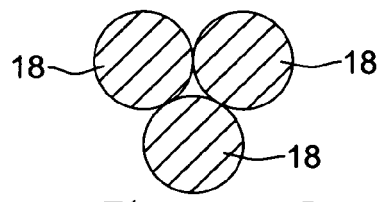
Figure 2C

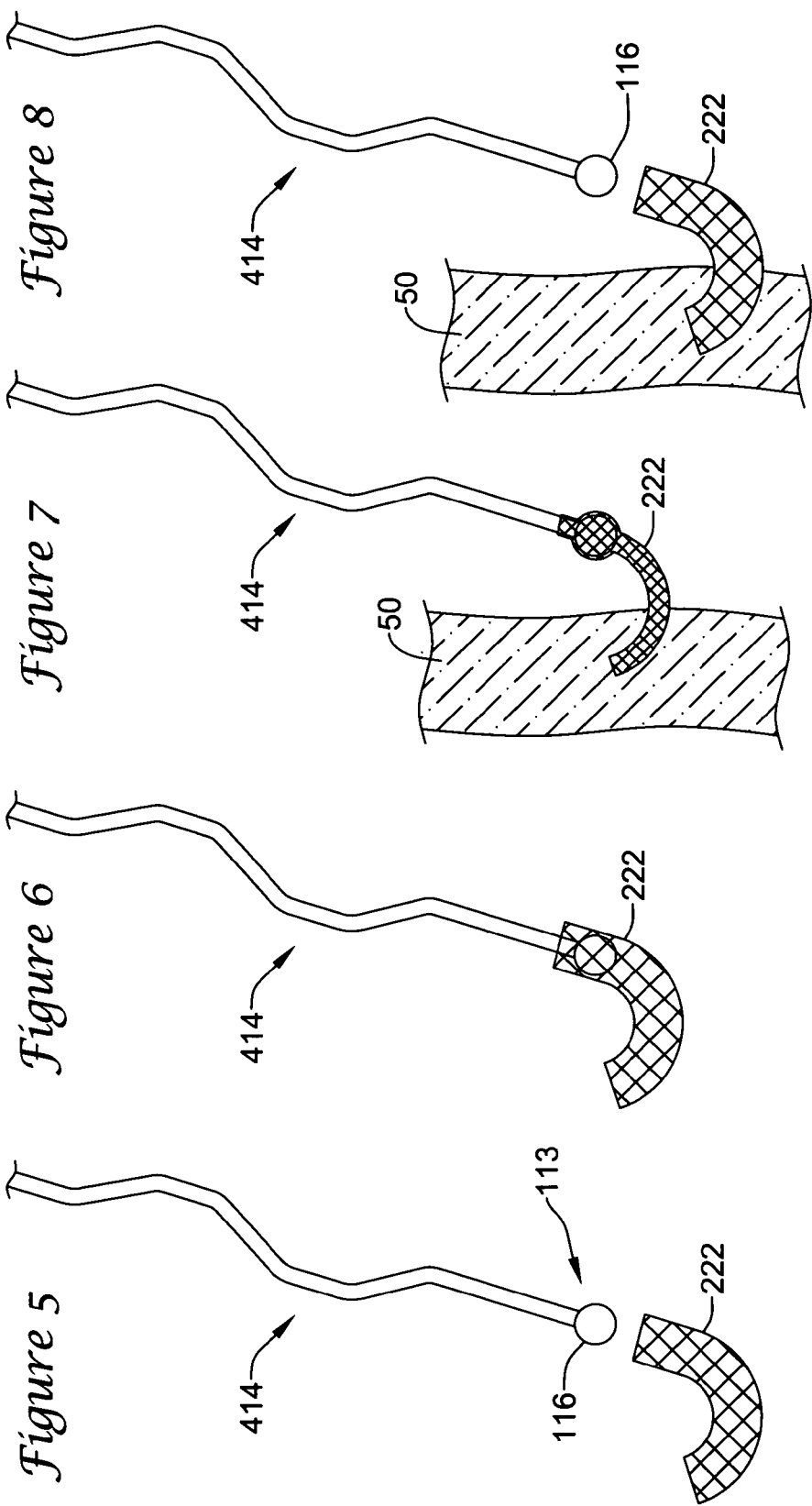

RETRIEVABLE VENA CAVA FILTER

FIELD OF THE INVENTION

The present invention pertains to the field of intra vena cava filters. In particular, the present invention pertains to retrievable intra vena cava filters. Intra vena cava filters are commonly implanted either temporarily or permanently in patients at risk for blood clotting.

BACKGROUND OF THE INVENTION

Blood clots (emboli) carried in the blood stream often constitute serious threats to health and in some instances, to life itself. The reduction of such clots, or their stabilization and arrest of further migration in the circulatory system of the body, is desiderata constantly motivating the development by the medical profession of new techniques and devices for this purpose. Although emboli moving in other portions of the circulatory system can also present serious problems, development of means for preventing emboli from migrating into the pulmonary circulation from the vena cava has received the primary attention.

One method of capturing emboli is the utilization of filters emplaced in the major blood vessels such as the vena cava. U.S. Pat. No. 4,817,600 to Herms et al. discloses a titanium filter having a plurality of legs joined to a head or nose bead; the legs having a first straight portion, and sharply divergent legs extending therefrom.

SUMMARY OF THE INVENTION

The present invention pertains to an intra vena cava filter implantable temporarily or permanently, and methods for removal thereof. The filter includes struts having tips that engage the wall of the vein or inner surface of another organ to provide positional stability of the filter.

In one embodiment, the struts are made of multiple wires, with the end of each wire sharpened and bent into a hook shape facing a different direction. In another embodiment, the expandable hooks are removed with the filter by reducing the diameter of the hooks. In a further embodiment, the filter includes expandable hooks that fit over the ends of the struts. The hooks function to secure the filter in a vessel, but can be expanded to release the struts, allowing removal of the filter. Methods are provided for subsequent removal of the filters.

BRIEF DESCRIPTION OF THE DRAWINGS

FIG. 2A is a side view of one strut of the filter of FIG. 1;

FIG. 2B is a side view of a strut of another embodiment of intra vena cava filter;

FIG. 2C is a cross-sectional view of the strut of FIG. 2A;

FIG. 5 is a side view of another embodiment of a strut with an expandable hook;

FIG. 6 is a side view of the strut of FIG. 5 with the expandable hook in the expanded configuration in position over the retaining member at the end of the strut;

FIG. 7 is a side view of the strut of FIG. 6 with the expandable hook in a radially contracted configuration secured to the end of the strut and embedded in the caval wall; and FIG. 8 is a side view of the strut of FIG. 7 with the expandable hook in an expanded configuration to release the strut for removal of the filter.

DETAILED DESCRIPTION OF THE INVENTION

Figure 1:
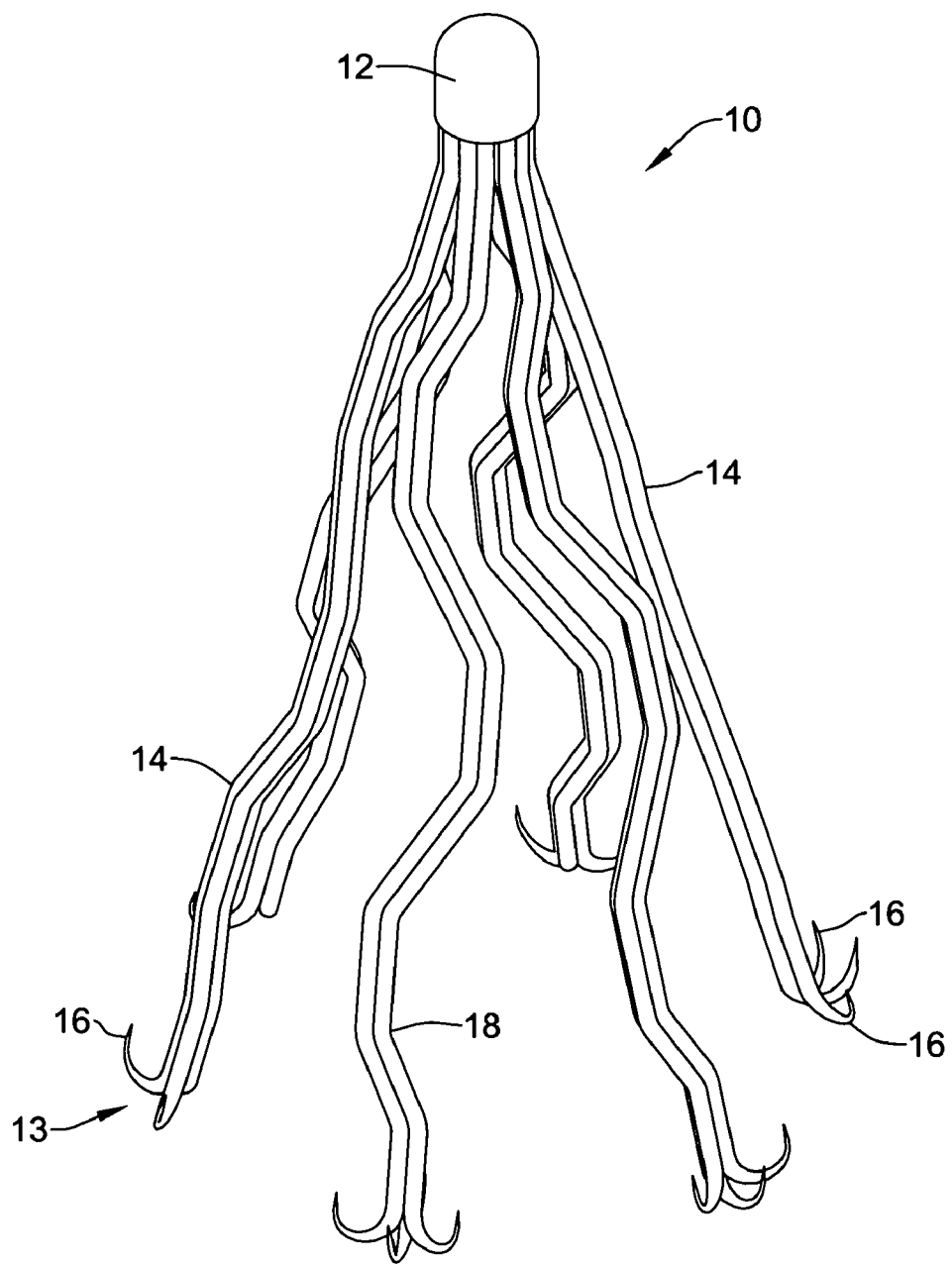
FIG. 1 is a front perspective view of an intra vena cava filter according to one embodiment of the invention.

Referring now to the drawings wherein like reference numerals refer to like elements throughout the several views, FIG. 1 is a front perspective view of a filter 10 including a hub 12 from which extends a plurality of legs 14. Each leg can be straight or can include bends or curves along its length. Bends or curves in the legs may help catch thrombi that flow through the vessel. In one embodiment, all of the legs 14 are identical. In another embodiment, some or all of the legs 14 are differently shaped. Some legs 14 can be straight while others have one or more bends, and the legs with bends can have different numbers of bends and the angles of the bends can be different. The legs 14 can be biased to expand from a radially compressed configuration in which some or all of the legs 14 are touching within a delivery device to the expanded, cone shaped configuration shown in FIG. 1, when deployed in a blood vessel.

The free end 13 of each leg 14 includes one or more barbs 16 for engagement with the vessel wall to stabilize filter 10 within a vessel. The barbs 16 can be integral with the legs 14 or the barbs 16 can be made separately and then attached to the free ends 13 of the legs 14. In one embodiment, each leg 14 is made of a plurality of wires 18. In the embodiment shown in FIG. 1, each leg 14 is made of three wires 18 attached to each other along their length. Each wire 18 has a barb 16 at the free end 13. The barbs 16 face in opposing directions. In another embodiment, the barbs 16 can face in substantially the same direction but are spaced apart. In a further embodiment, each leg is formed of a single wire that is split or divided into a plurality of barbs at the free end. The barbs 16 are configured to anchor the filter to the vessel walls.

The legs 14 and hub 12 can be made of the same material or can be made of different materials. Suitable materials include metals such as platinum, gold, tantalum, tungsten, titanium, or metal alloys such as stainless steel, Beta III Titanium, cobalt-chrome alloy, Elgiloy®, L605, MP35N, and Ta-10W. In one embodiment, the legs 14 and hub 12 are made of biocompatible titanium alloy beta III (ASTM grade 10, obtained from Ormco Corporation of Glendora, Calif., and designated Ti-11.5Mo-6Zr-4.5Sn, with major alloy elements molybdenum (10-13%), Zirconium (4.5-7.5%) and Tin (3.75-5.25%))

The legs 14 can be made of a plurality of wires, ribbons, threads, rods, filaments, etc. In one embodiment, the legs 14 are made of a bundle of three wires. The wires 18 can be attached along their entire length, as shown in FIGS. 1, 2A and 2C. In another embodiment the wires 18 are attached to each other at one or more discrete points 20 along their length. In the embodiment shown in FIG. 2B, a leg 114 is formed of three wires 18 spaced apart between the attachment points 20. The wires can be attached by adhesive, and solder. In one embodiment, legs 14 are made of wire having a diameter of about 0.018 inch (0.5 mm).

The legs 14 extend outward from the hub 12 to define an imaginary cone. In one embodiment, the hub 12 is formed by fusing the legs 14 together. In a further embodiment, the hub 12 is a separate element attached to the legs 14. The hub 12 can have any shape, including a sphere, cylinder, oval, polygon, etc. In some embodiments, the legs 14 include multiple angles, as shown in FIG. 1. In one embodiment, the diameter of the base of the filter is about 38 mm, and the overall length of the filter is about 50 mm.

Figure 3A:
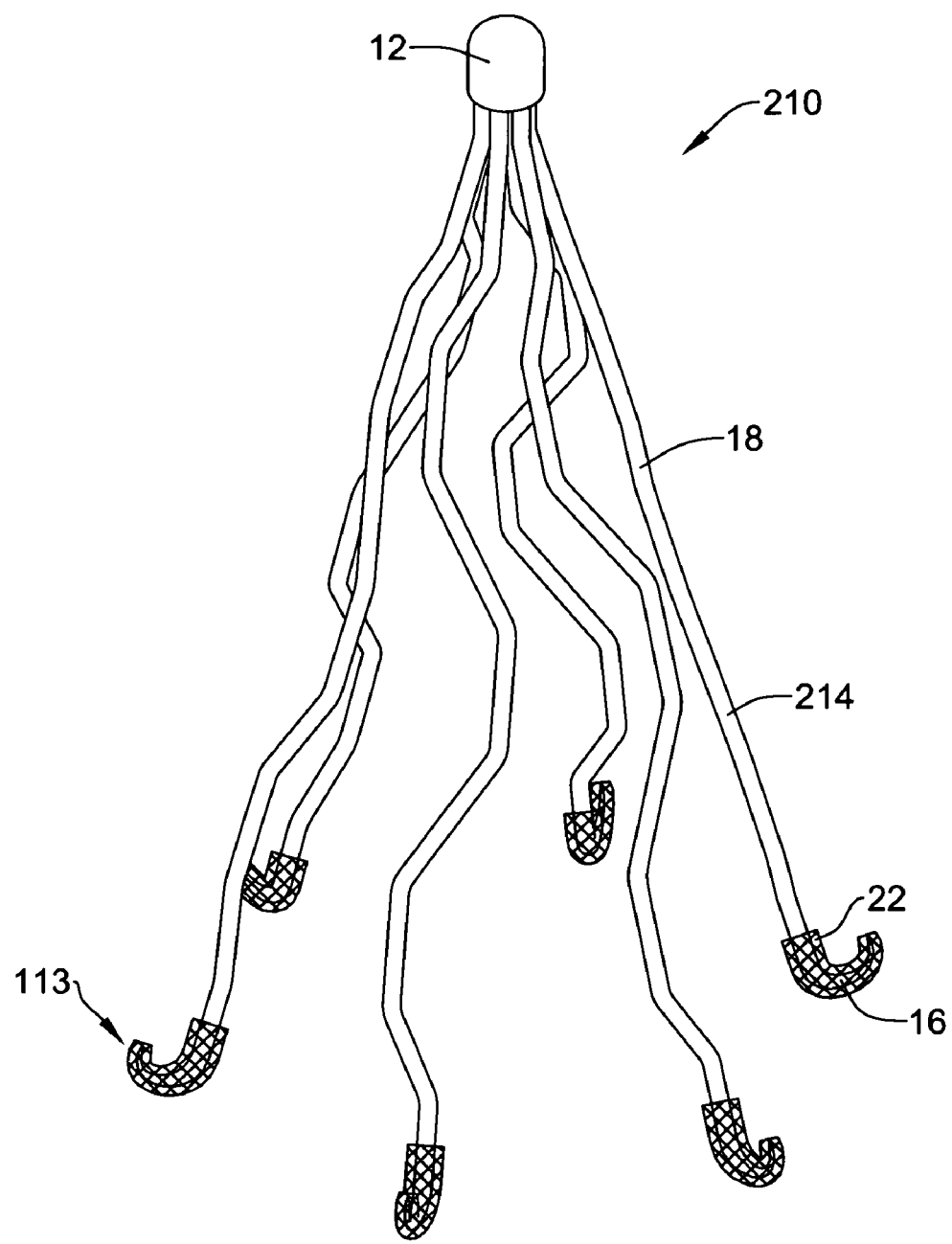
FIG. 3A is a front perspective view of an intra vena cava filter according to another embodiment of the invention.
Figure 3C:
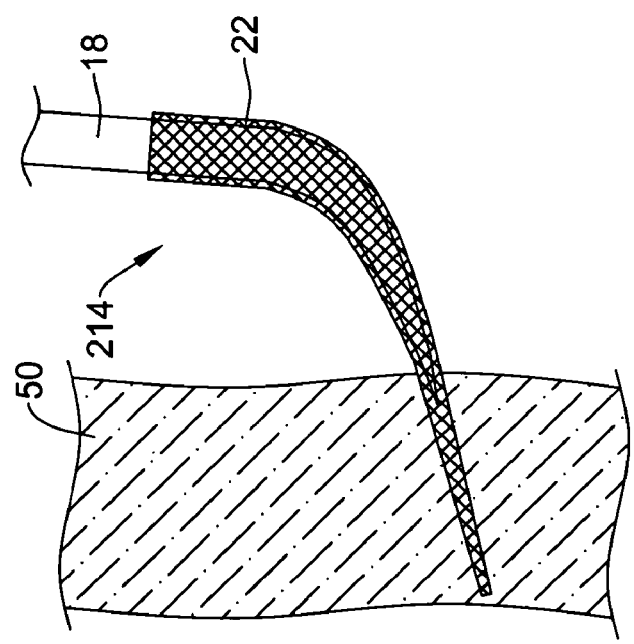
FIG. 3C is a side view of the strut end of FIG. 3B with the radially contractible sleeve in an extended, radially contracted configuration as the strut is removed from a vessel wall.
Figure 3B:
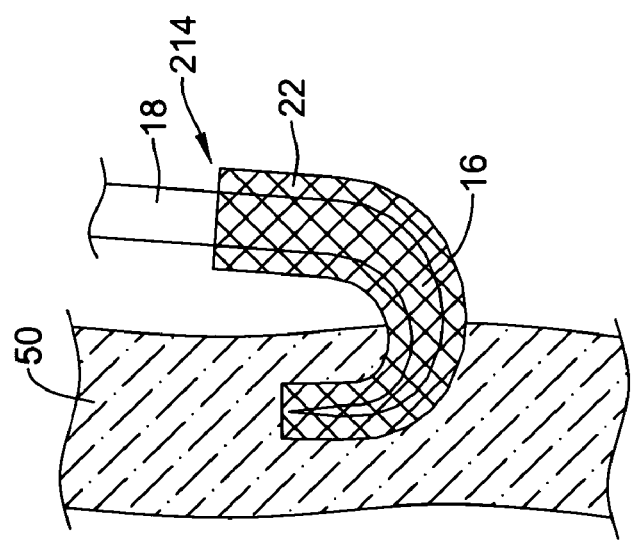
FIG. 3B is a side view of a strut end and radially contractible sleeve of the filter of FIG. 3A embedded in a vessel wall.

In a further embodiment, shown in FIGS. 3A-3C the filter 210 includes radially contractible sleeves 22 attached to one or more legs 214. The radially contractible sleeve 22 fits over the barb 16 and is attached to the free end 113 of the leg 214. The sleeve 22 can be made of a mesh, braid, net, or woven material. As used herein, woven material is intended to include a plurality of strands that are interlaced, twisted, knotted, braided, knitted, or otherwise interconnected to form a material that contracts and expands radially and in a lengthwise direction. In one embodiment, the sleeve 22 is made of Nitinol. In the radially expanded state, shown in FIG. 3B, the sleeve 22 diameter is larger than the diameter of the barb 16. In the radially contracted state, shown in FIG. 3C, the sleeve 22 extends lengthwise and fits tightly around the barb 16. In use, the filter 210 is delivered to the desired vessel location with the sleeves 22 in a radially expanded state covering barbs 16 of the legs 214. The sleeve-covered barbs 16 are embedded in the vessel walls 50 to anchor the filter 210, as shown in FIG. 3B. When the filter 210 is to be retrieved, the legs 214 are pulled, causing the sleeves 22 to extend and radially contract around the extended barbs 16, reducing their diameter and allowing the barbs 16 to be removed from the vessel wall 50, as shown in FIG. 3C. After a filter has been in place for a period of time, endothelial growth over the barbs often makes removal difficult. The ability of the sleeve 22 to radially contract reduces its diameter and allows the filter 210 to be removed even after endothelial growth occurs over the sleeve 22.

Figure 4:
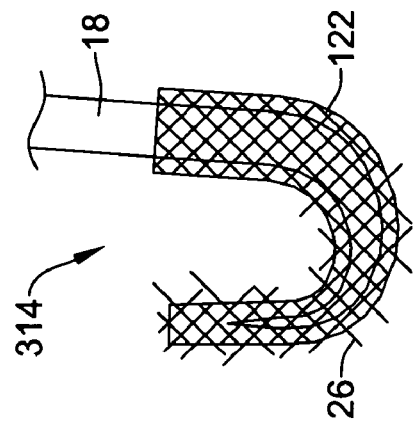
FIG. 4 is a side view of another embodiment of radially contractible sleeve.

In a further embodiment, the radially contractible sleeve 122 has a plurality of projections 26, as shown in FIG. 4. The projections 26 can be extensions of wires, threads, ribbons, etc. that form the net, mesh or woven radially contractible sleeve 122. In another embodiment, the projections 26 are additional wires, threads, ribbons, etc. attached to the exterior of the sleeve 122. The projections 26 may help anchor the sleeve within the vessel wall 50.

Another embodiment of the invention is shown in FIGS. 5-8. This embodiment is similar to the embodiment shown in FIG. 3A except that instead of a barb, the free ends 113 of the legs 414 have a retaining member 116. An expandable hook 222 fits over and is secured to the retaining member 116. The expandable hook 222 anchors the filter to the vessel wall 50, as shown in FIG. 7. The retaining member 116 can be configured as a sphere, as shown in FIGS. 5-8, or any other shape that provides a surface to which the expandable hook 222 can be secured. Other such shapes include a square or other polygon, a triangle, an oval, etc.

The expandable hook 222 is radially expandable and fits over the retaining member 116 at the free end 113 of each leg 414. Once the expandable hook 222 is positioned over the retaining member 116, the hook 222 is radially contracted around the retaining member 116 thereby securing the hook 222 to the leg 414. The expandable hook 222 can be made of a mesh, braid, net, or woven material. In one embodiment, the expandable hook 222 is made of Nitinol. The expandable hook 222 can be expanded and contracted by changing the temperature of the hook. In another embodiment, the expandable hook 222 is mechanically expanded and contracted. In further embodiments, the expandable hook 222 is expanded and contracted via a chemical reaction.

In the radially expanded state, shown in FIGS. 5 and 6, the diameter of the expandable hook 222 is larger than the diameter of the retaining member 116. In the radially contracted state, shown in FIG. 7, the expandable hook 222 extends lengthwise and contracts tightly around the retaining member 116. In use, expandable hooks 222 are attached to retaining members 116 at the free ends 113 of at least two filter legs 414. See FIGS. 5 and 6. The hooks 222 are contracted around the retaining members 116, and the filter is delivered to the desired vessel location where the expandable hooks 222 are embedded in the vessel walls 50, as shown in FIG. 7. If the filter is to be retrieved, the hooks 222 are expanded, as shown in FIG. 8, thereby releasing the retaining members 116 and allowing the filter to be retrieved. The hooks 222 remain in the vessel wall 50.

The filter 10, 210 can be placed within a vessel by way of a jugular vein access point or other intravascular route as known to those skilled in the art. It is anticipated that the filter disclosed herein can be placed permanently in the vena cava or other organ, as well as being placed temporarily.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A filter device positionable within a blood vessel for trapping emboli, the device comprising:
   a plurality of divergent legs having first and second ends, wherein the legs are secured at their first ends to each other and each leg has at least two barbs at the second end;
   wherein each leg is formed of a plurality of wires, at least two of the plurality of wires having a barb at the second end of the leg; and
   wherein the plurality of wires are fixedly attached to each other along substantially their entire length.

2. The filter device of claim 1, wherein the legs are formed of nitinol.

3. The filter device of claim 1, wherein each wire has a barb at the second end of the leg.

4. The filter device of claim 1, wherein each leg is formed of three wires bonded together, wherein each wire has an outwardly facing barb at the second end of the leg.

5. The filter device of claim 1, wherein each leg includes a first linear portion emanating distally from the first end, a second, multi-angled portion, and a third linear portion including the barbs.

6. The filter of claim 1, wherein the first ends of the legs are fused together to form an apical head.

7. The filter of claim 1, further comprising an apical head, wherein the first ends of the legs are attached to the head.

8. A filter device for trapping emboli, the device comprising:
   a plurality of divergent legs having proximal and distal ends, wherein the legs are secured at their proximal ends to each other and each leg has at least two barbs at the distal end;
   wherein each leg is formed of a plurality of wires, at least two of the plurality of wires having a barb at the distal end of the leg;
   wherein the plurality of wires are fixedly attached to each other at a first location adjacent the proximal end, are fixedly attached to each other at a second location adjacent the distal end, and are fixedly attached to each other at a third location between the legs proximal and distal ends; and wherein at least two of the barbs on at least one of the leg extend in different directions;

wherein the proximal ends of the plurality of legs are attached to an apical head, the plurality of legs extending conically outward from the apical head to the distal ends.

9. The filter device of claim 8, wherein the legs are formed of nitinol.

10. The filter device of claim 8, wherein each wire has a barb at the distal end of the leg.

11. The filter device of claim 10, wherein the plurality of wires are attached to each other along substantially their entire length.

12. The filter device of claim 8, wherein each leg is formed of three wires bonded together, wherein each wire has an outwardly facing barb at the distal end of the leg.

13. The filter device of claim 12, wherein the wires are bonded together at one or more discrete locations along a length of the leg.

14. The filter device of claim 13, wherein the wires are spaced apart between the bonded locations.

15. The filter device of claim 8, wherein each leg includes a first linear portion emanating distally from the proximal end, a second, multi-angled portion, and a third linear portion including the barbs.

16. The filter of claim 8, wherein the proximal ends of the legs are fused together to form the apical head.

* * * * *